United States Patent [19]
Kawai et al.

[11] Patent Number: 5,640,436
[45] Date of Patent: Jun. 17, 1997

[54] METHOD AND APPARATUS FOR X-RAY COMPUTED TOMOGRAPHY

[75] Inventors: Hiroyuki Kawai, Tokyo; Kensuke Sekihara, Musashimurayama, both of Japan

[73] Assignee: Hitachi Medical Corporation, Tokyo, Japan

[21] Appl. No.: 588,918

[22] Filed: Jan. 19, 1996

[30] Foreign Application Priority Data

Jan. 26, 1995 [JP] Japan .................................. 7-010322
Jun. 22, 1995 [JP] Japan .................................. 7-155694

[51] Int. Cl.$^6$ ....................................................... A61B 6/03
[52] U.S. Cl. ............................................... 378/4; 378/901
[58] Field of Search ........................ 378/4, 901; 364/413, 364/18

[56] References Cited

U.S. PATENT DOCUMENTS 5,493,593  2/1996  Muller et al. ............................... 378/4

OTHER PUBLICATIONS

SPIE Vol.2163, Physics of Medical Imaging, pp.199–210, 1994.
JP-A-5-28316(U) Japan Filing Date Sep. 27, 1991 Translation Not avail.
J.Opt.Soc.Am. A/vol.1, No.6, Jun. 1984, pp.612–619.
Medical Physics, vol.6, No.5, pp.412–417, 1979.

*Primary Examiner*—David P. Porta
*Assistant Examiner*—David Vernon Bruce
*Attorney, Agent, or Firm*—Antonelli, Terry, Stout & Kraus, LLP

[57] ABSTRACT

A method for X-ray computed tomography includes a process for rotating around an object an X-ray source for applying a cone-beam X ray and a scanner having a two-dimensional X-ray detector mounted thereon for deriving projection data and a process for preparing a geometric distortion correction table for correcting an image geometric distortion of the two-dimensional X-ray detector for the projection data, for reconstructing a distribution of X-ray attenuation coefficients of the object from said corrected projection data. The method further includes a process for calculating a function for evaluating the correction table, a process for comparing the calculated value with a threshold value, a process for correcting the correction table through the interpolation based on the compared result, a process for correcting an image geometric distortion of the projection data by using the corrected table, a process for detecting a location of a view field boundary of the detector from the distortion-corrected projection data, and a process for generating the projection data of a predetermined width from the detected location of the view field boundary through the effect of the extrapolation. The method operates to reconstruct a distribution of X-ray attenuation coefficients of the object from the extrapolated projection data.

30 Claims, 8 Drawing Sheets

MISSING PORTION    MISSING PORTION

EXTRAPOLATED PORTION    EXTRAPOLATED PORTION

METHOD AND APPARATUS FOR X-RAY COMPUTED TOMOGRAPHY

BACKGROUND OF THE INVENTION

The present invention relates to a method and an apparatus for cone-beam X-ray computed tomography that include an X-ray source for applying a cone-beam X ray, a two-dimensional X-ray detector for detecting the X ray and a scanner having the detector mounted thereon so that the scanner is rotated around an object to be inspected (hereafter simply called an object) for measuring the data projected from multiple points located around the object and reconstructing a distribution of X-ray attenuation coefficients of the object based on the measured data. FIG. 2 shows a common arrangement of the conventional cone-beam X-ray computed tomography. The conventional cone-beam X-ray computed tomography is arranged to have a measuring unit 1, a data processing unit 2 for processing the measured data, and a unit 18 for preparing geometric distortion correction table. On a scan mechanism 3, an X-ray source 4 is located as opposed to a two-dimensional detector 5 such as an X-ray image intensifier (I. I.) with an object 6 laid midway between the X-ray source 4 and the detector 5. The X-ray source 4 operates to apply a cone-beam X ray 7 to the object 6. The two-dimensional detector 5 operates to detect an intensity of the X ray passed through the object 6. The scan mechanism 3 is measuring the intensity of the X ray passed through the object with the detector 5 as it is rotating around the object 6.

The measured data is digitized and then is sent to the data processing unit 2. The data processing unit 2 operates to correct adverse effects applied on the measured data by a dark current bias and a non-uniform distribution of sensitivity of the detector and logarithmic-transform the corrected data into the projection data in a pre-processing unit 9. This logarithmic transformation is the same as the transformation performed by the conventional fan-beam X-ray computed tomography. Next, a geometric distortion correction unit 10 operates to correct the geometric distortion using the geometric distortion correction table. The geometric distortion basically depends on the characteristic of the two-dimensional detector 5. Of the candidate detectors, the image intensifier may bring about a pincushion distortion far remarkably than any other detector. The occurrence of the pin cushion distortion results from the spherical input surface of the image intensifier. If the projection data contains the geometric distortion, the data does not allow the precise reconstruction of the distribution of the X-ray attenuation coefficients. Hence, the correction for the image geometric distortion is an indispensable pre-processing step. In place, the correction for the image geometric distortion may be executed for the measured data before correcting the adverse effects caused by the dark current bias and the non-uniform distribution of sensitivity of the detector or performing the algorithmic transformation. As an example of the aforementioned geometric distortion correcting method, please refer to the writing: R. Ning, et al. "An Image Intensifier-based Volume Tomographic Angiography Imaging System: Geometric Distortion Correction, (SPIE Vol.2163, Physics of Medical Imaging, pp.199–210, 1994) or the Japanese unexamined laid-open No. Hei 5-28316 (JP-A-5-28316).

On the overall projection data formed by the foregoing pre-processing, the image reconstructor 11 operates to reconstruct a three-dimensional distribution of attenuation coefficients of the object 6 within a field of view. This three-dimensional reconstructed data is subject to a volume rendering process or an imaging process like a maximum intensity projection process in the rendering unit 12. As this kind of reconstructing operation, a Feldkamp's cone-beam reconstructing operation is known. (see the publication: L. A. Feldkamp et al., "Practical Cone-beam Algorithm", J. Opt. Soc. Am. A, Vol.1, No.6, pp. 612–619, 1984).

Of the foregoing processes, the correction for geometric distortion will be discussed in detail. If the image intensifier is used as the two-dimensional detector 5, the typical geometric distortion appears as shown in FIG. 6. The image shown in FIG. 6 is obtained by fixing to the front of the detector (image intensifier) 5 a metal plate having pin holes opened at regularly spaced lattice points as shown in FIG. 7 and imaging a projected image. Such a metal plate is called a hole chart 19. The projected image picked by the above process is called a hole chart projected image. This geometric distortion results from a composite of some causes. The first cause is a geometric distortion of the measuring system. The second cause is a nonplanar input surface of the detector 5. In particular, if the detector 5 uses the image intensifier, the spherical input surface of the image intensifier brings about the pincushion distortion in the projection data. The third cause is a deviation of an electron beam of an electronic camera system contained in the image intensifier, the deviation being caused by an external magnetic field such as geomagnetism.

As a method for correcting an image geometric distortion, it is possible to refer to the correcting method built in the technique known as a realtime DR (Digital Radiograph) that uses the image intensifier as the detector 5. The correction for the image geometric distortion is executed by referring to the geometric distortion correction table. This table is saved in the memory 20 for saving geometric distortion correction table. Later, the description will be oriented to the conventional image geometric distortion correcting method arranged to refer to the correction table. The projected image (containing the image geometric distortion) is represented as Pd(U, V). The projected image from which the image geometric distortion is removed is represented as P(u, v). Between both of the images, the relation of P(u, v)=Pd(U(u,v), V(u, v)) is set up, in which the functions U (u, v) and V (u, v) represent the image geometric distortion. In actual, the variables u and v assume discrete values. Hence, these functions U and V are put into a table, then the image geometric distortion is corrected by looking up the table. This table corresponds to a geometric distortion correction table. More particularly, the image geometric distortion correction is executed by preparing the table U (u, v) and V (u, v) in which (u, v) are assumed as pixel coordinates like u=1, 2, ..., $N_i$ and v=1, 2, ..., $N_j$ and deriving P (u, v) by the four-point Lagrange's interpolation as indicated in the expression (1).

$$\begin{aligned}P(u,v) = \ &(1 - U(u,v) + U)(1 - V(u,v) + V) \cdot Pd(U,V) + \\ &(U(u,v) - U)(1 - V(u,v) + V) \cdot Pd(U+1,V) + \\ &(1 - U(u,v) + U)(V(u,v) - V) \cdot Pd(U,V+1) + \\ &(U(u,v) - U)(V(u,v) - V) \cdot Pd(U+1,V+1)\end{aligned} \quad (1)$$

where U and V are the maximum integers that do not surpass U(u, v) and V(u, v), respectively.

The geometric distortion correction table U(u, v) and V(u, v) is generated by using the foregoing hole chart projected image in the geometric distortion correction table generator 21. The generation of the correction table will be executed as follows. The prepared geometric distortion correction table is saved in the memory 20 for geometric distortion correction table. At first, the pin hole locations are extracted from the hole chart projected image. For the extraction, a proper image recognition technique is used. In the hole chart projected image, as shown in FIG. 7, a pin hole at the i-th dot in the u direction and the j-th dot in the v direction is represented as $h_{ij}$, the location of which is represented as $(u_{ij}, v_{ij})$. In actual, as shown in FIG. 7, the pin holes are not allowed to be at the respective lattice points. For the explanation's sake of convenience, it is assumed that the pin holes are located at the respective lattice points. In the projected image containing the image geometric distortion, the pin hole for the pin hole $h_{ij}$ is $H_{ij}$ and is located at $(U_{ij}, V_{ij})$. Through the effect of the foregoing functions $U(u, v)$ and $V(u, v)$, the image geometric distortion correction table at this lattice point, that is, the pin hole location is represented as $U_{ij}=U(u_{ij}, v_{ij})$ and $V_{ij}=V(u_{ij}, v_{ij})$. The other points except this lattice points (pin hole locations) are defined by the four-point Lagrange's interpolation as indicated in the expression (2). Assuming that $u=1, 2, \ldots, N_i$ and $v=1, 2, \ldots, N_j$, the geometric distortion correction table values $U(u, v)$ on all the points $(u, v)$ are defined. The similar operation is performed with respect to $V(u, v)$.

$$\begin{aligned}
U(u,v) = \ & (1 - U_{ij} + U)(1 - V_{ij} + V) \cdot U(u_{ij},v_{ij}) + \\
& (U(u,v) - U)(1 - V(u,v) + V) \cdot \\
& U(U_{i+1,j}, V_{i+1,j}) + \\
& (1 - U(u,v) + U)(V(u,v) - V) \cdot \\
& U(U_{i,j+1}, V_{i,j+1}) + \\
& (U(u,v) - U)(V(u,v) - V) \cdot \\
& U(U_{i+1,j+1}, V_{i+1,j+1})
\end{aligned} \quad (2)$$

wherein U and V are maximum integers that do not surpass $U_{ij}$ and $V_{ij}$, respectively.

In the cone-beam X-ray computed tomography apparatus, to correct the image geometric distortion, the foregoing geometric distortion correction is executed for the overall projection. In addition, the geometric distortion correction table is generated at least once when the cone-beam X-ray computed tomography apparatus is installed and then at a routine maintenance time.

The foregoing conventional cone-beam X-ray computed tomography apparatus has two shortcomings. One of them is a small field of view of the two-dimensional X-ray detector (simply called a detector), and the other one is a requirement for a massive amount of data for preparing a geometric distortion correction table.

At first, the description will be oriented to the shortcoming resulting from the small field of view of the detector.

In the foregoing conventional apparatus, the field of view of the detector 5 is not large enough to cover the overall object 6. For example, consider that the detector 5 uses the image intensifier. The image intensifier does not have so long a diameter of a plane of incidence. Concretely, it is about ten and some inches (about 30 cm). The object reflected in the field of omnidirectional projections is basically a small spherical region whose diameter is as short as about 20 cm, though the actual region depends on the geometry of the overall measuring system. This restriction of the field of the detector 5 truncates the peripheral portion of the object from the projection data. The projection data with the portion truncated from the actual object is applied to the foregoing Feldkamp's cone-beam reconstructing operation for reconstructing the three-dimensional reconstructed data. In this three-dimensional data, the X-ray attenuation coefficients around the region boundary of the field are made higher than the actual attenuation coefficients, while the attenuation coefficients in the central region of the field are made lower. That is, a shading artifact phenomenon takes place. This reconstructed data does not exactly represent the distribution of the X-ray attenuation coefficients of the object 6, on which data no right diagnosis is allowed. One of the methods for avoiding this shortcoming is that the field of the detector 5 is made large enough to cover the overall object 6. In actual, however, it is difficult to realize the detector 5 with so large a field. The region of interest substantially required for the actual diagnosis is not so large. Hence, if the detector 5 may has a large field of view, the resulting X-ray computed tomography apparatus is made so large in scale and needs a larger amount of calculations. Such an apparatus is not realistic.

In order to avoid occurrence of the shading artifact phenomenon, therefore, it is necessary to realize the method for reconstructing an exact distribution of X-ray attenuation coefficients in the region of interest from the incomplete projection data, that is, the data that does not contain the data about the portion of the object departed from the field of the detector. To realize this kind of method, various studies have been tried. (For example, refer to the writing: R. M. Lewitt., Processing of Incomplete Measurement Data in Computed Tomography, Medical Physics, Vol.6, No.5, pp.412–417, 1979.) The Lewitt's truncation correction is a method for compensating for the data about the portion cut out of the projection data through the effect of the extrapolation. The extrapolation needs information about a rough contour of the object. The contour is assumed as a relatively simple form like an ellipse or measured by a sensor. However, the truncation correction used in the fan-beam X-ray computed tomography is not straightforward applicable to the cone-beam X-ray computed tomography to which the present invention applies. The causes therefor are as follows.

The first cause is a curved surface of incidence of the image intensifier. Further, the influence of geomagnetism does not stabilize the boundary of the field of the detector 5 on the projection data. It is hence difficult to distinguish a site of the object located within the field of the detector 5, that is, the site about which the exact data is measured, from another site of the object outside the field, that is, the site about which the inexact data is measured. As mentioned above, the cone-beam X-ray computed tomography apparatus supplies the projection data after temporarily correcting the geometric distortion of the measured data obtained by the detector 5. The projection data that was subject to the geometric distortion correction does not correspond to the measured data at a one-to-one ratio. Further, the image geometric distortion indicates a pattern varied at each projection (angle). Therefore, on the projection data whose geometric distortion is corrected, the boundary of the field is made variable at projections (angles). On the other hand, the fan-beam X-ray computed tomography apparatus supplies the projection data that corresponds to the data measured by the X-ray detector array at a one-to-one ratio. Therefore, the boundary of the field on the projection data straightforward corresponds to the both ends of the X-ray detector array. It means that the fan-beam X-ray computed tomography apparatus does not have the foregoing shortcoming.

The second cause is difficulty in presuming or measuring the contour of the object. The region of interest to be imaged covers various sites of the object such as a head, a thorx, an abdomen and a pelvis, and each object is different. Hence, it is not easy to presume the contour of the object. Several patterns of the contours may be prepared for allowing the most approximate one to the region of interest of the object to be selected. In this case, the data on which the pattern is selected has to be read by an operator' manual operation, a sensor or the like. Besides, the measurement of the contour for each object makes the overall apparatus idly complicated, and it is not realistic.

The detector 5 like the image intensifier may selectively have a field of view in imaging the object. For a small region of interest, the field of view may be adjusted to be smaller for improving spatial resolution. It is hence desirable to select the truncation correction method, because this method may easily cope with change of a field size if the detector 5 is required to switch the field size when imaging the object.

Next, the description will be oriented to the second shortcoming about a geometric distortion correction table. As mentioned above, the cone-beam X-ray computed tomography apparatus may use the geometric distortion correction method built in the realtime DR technique for the geometric distortion correction for the measured data. In actual, however, the cone-beam X-ray computed tomography needs to process a massive amount of data. Hence, the straightforward application of this correction method may bring about the shortcoming. The first cause (geometric distortion of the measuring system) and the second cause (nonplanar measuring surface of the detector 5), which have been described above as the causes for bringing about the image geometric distortion, do not depend on the direction of the detector 5, that is, the projection angle. However, the image geometric pattern based on the third cause (variable deviation of an electron beam of the electron camera system provided in the image intensifier) varies at each projection angle. It indicates that this correction method needs to prepare the geometric distortion correction tables for all the projection angles. That is, the hole chart projection image is required to be picked at every projection angle. To execute it, however, the following problem rises.

In general, the cone-beam X-ray computed tomography needs to take a hundred to several hundred of images. The conventional fan-beam X-ray computed tomography has already provided the image reconstruction based on more than hundreds of projection images. The cone-beam X-ray computed tomography is often required to process such a number of images. In any case, the cone-beam X-ray computed tomography needs to take such many images and process a massive amount of data. Hence, a certain kind of data abnormality probably takes place in the processing of a signal at the measuring time, transmission of a signal, internal or external storage means or data transfer between storage means (memories). If the data abnormality appears on the hole chart projection image, the abnormality stops to generate the exact geometric distortion correction table. For example, inclusion of noise causes a pin hole to be erroneously recognized at a spot where no pin hole is located. Even one erroneously recognized pin hole may greatly impair the geometric distortion correction table generated on the pin hole. If the geometric distortion correction table is not exactly generated, no exact geometric distortion of the projection data is expected. Hence, the three-dimensional image is not exactly reconstructed.

As means for solving the foregoing problem, improvements for suppressing the abnormality on the image data are added to the measuring system, the signal processing system, the signal transmitting system, the information storage means, and the like. However, these improvements needs to overall or partially redesign the apparatus. This results in making the apparatus more costly. Further, however sophisticated the prepared hardware may be, complete avoidance of abnormal data is impossible.

As means for solving the problem, hence, it is desirable to check if the geometric distortion correction table is exactly generated and replace the table with missing data with a right one at the post-processing step.

SUMMARY OF THE INVENTION

It is a first object of the present invention to provide a method and an apparatus for cone-beam X-ray computed tomography that are arranged to overcome the foregoing first shortcoming the prior art involves and realize the processes (1) of detecting the field boundary on the projection data at every projection angle and (2) of stably treating data without having to depend on the contour and the size of the object 6 and the field size of the detector 5 when imaging the object as a truncation correction method.

In a cone-beam X-ray computed tomography method of reconstructing a distribution of X-ray attenuation coefficients of the object by using projection data measured in the omnidirectional projections of the object by rotating a scanner mounting an X-ray source for applying a cone-beam X ray and a two-dimensional X-ray detector for detecting the X-ray, the first object of the invention is achieved by an X-ray computed tomography method including the steps of correcting an image geometric distortion of the projection data, detecting a field boundary from the projection data whose geometric distortion is corrected, generating the projection data of a certain width from the detected field boundary through the effect of an extrapolating calculation, and reconstructing the distribution of X-ray attenuation coefficients of the object from the extrapolated projection data.

Further, the first object of the invention is achieved by an X-ray computed tomography apparatus arranged to have a scanner mounting an X-ray source for applying a cone-beam X ray and a two-dimensional X-ray detector and rotate the X-ray source and the scanner around an object for measuring the data of the omnidirectional projections around the object and reconstructing the distribution of the X-ray attenuation coefficients of the object based on the projection data, which apparatus includes a unit for correcting an image geometric distortion of the projection data, a unit for detecting a field boundary of the projection data whose geometric distortion is corrected by the correcting unit, an extrapolating unit for generating the projection data of a certain width from the detected field boundary, and a unit for reconstructing the distribution of the X-ray attenuation coefficients of the object from the projection data extrapolated by the extrapolating unit.

It is a second object of the present invention to provide a method and an apparatus for X-ray computed tomography which are arranged to overcome the foregoing second shortcoming the prior art involves and to generate the exact geometric distortion correction tables at every projection angle without having to improve the apparatus itself.

The second object of the present invention is achieved by a method for cone-beam X-ray computed tomography, which includes in the step of generating a geometric distortion correction table for correcting a peculiar geometric distortion to the detector a step of generating a geometric distortion table, a step of temporarily saving the geometric distortion table, a step of calculating an evaluation function for evaluating the geometric distortion table, a step of comparing a calculated value of the evaluation function with a predetermined threshold value, and a step of generating a geometric distortion correction table through the effect of the interpolation.

Further, the second object of the present invention is achieved by an apparatus for cone-beam X-ray computed tomography, which includes in a unit for preparing a geometric distortion correction table for correcting a peculiar geometric distortion to a two-dimensional detector a unit for generating a geometric distortion correction table, a unit for temporarily saving the geometric distortion correction table, a unit for calculating an evaluation function for evaluating the geometric distortion correction table, a unit for comparing the calculated value of the evaluation function with a predetermined threshold value, and an interpolating unit for preparing the geometric distortion correction table through the effect of the interpolation.

The method and apparatus for X-ray computed tomography according to the present invention are arranged to compensate the projection data for a truncated projection of an object through the effect of the extrapolation. In order to meet the aforementioned two conditions required by the truncation correction method used in the cone-beam X-ray computed tomography, the method and the apparatus according to the invention include the steps of (1) setting zero or a special value for the out of a view field to a region of the projection data for the out of a view field of the detector 5, (2) detecting a location of a view field boundary by scanning the projection data, and (3) extrapolating the projection data of a certain width from the detected location of the view field boundary to the out-of-field region.

Along these processes, the method and the apparatus according to the present invention enable to avoid the artifact phenomenon on the reconstructed data resulting from the portion of the object truncated from the view field of the detector without having to add further components like a sensor when reconstructing the image or calculate a large amount of load.

That is, the method and the apparatus according to the present invention enable to avoid the artifact phenomenon without having to add further instruments or operations under variable imaging conditions in which the region of interest and the location of the object 6 is variable, each object is different, the field size of the detector 5 is variable in imaging the object, and the like.

Moreover, the method and the apparatus according to the present invention operate to check the geometric correction table and re-prepare the exact geometric correction table, as indicated below, for solving the foregoing problem that the geometric distortion correction table is not exactly generated.

The geometric distortion correction table is generated from the hole chart projection image at every projection angle. The table is generated at each projection angle according to the foregoing geometric distortion correction table preparing method. The generated geometric distortion correction table is checked. Concretely, the geometric distortion correction table of the object projection angle of interest is compared with the geometric distortion correction tables before and after the correction table of interest. If the discontinuous change between the correction tables is found, the correction table is removed. In place of the removed correction table, a new correction table is interpolated from the correction tables before and after the removed table and then is replaced with the removed table.

According to the present invention, as such, the exact geometric distortion correction table at every projection angle may be obtained by a simple method without having to redesign all or part of the apparatus.

At first, the conventional geometric distortion correction table preparing process is applied to the hole chart projection image at every projection angle for obtaining the geometric distortion correction table at every projection angle. Then, the continuity between the correction tables at the adjacent projection angles is checked for determining if the correction table is exactly prepared. If it is not, in place of the inexact correction table, a new geometric distortion correction table is interpolated from the correction tables before and after the inexact correction table and then is replaced with the inexact one. After these series of processes, the exact geometric distortion tables at all projection angles are prepared.

As set forth above, the method and the apparatus for X-ray computed tomography according to the present invention realizes as the truncation correction method for the cone-beam X-ray computed tomography the processes of (a) sensing a location of a view field boundary on the projection data at each projection and (b) keeping the correction independent of the contour form and the size of the object and the size of an imaging field of the detector. More particularly, the method and the apparatus enable to avoid the artifact phenomenon on the reconstructed data resulting from the portion of the object truncated out of the view field of the detector. The method and the apparatus according to the invention perform an extrapolation about the imaged projection data for compensating the projection data for the truncated portion. This makes it possible to avoid the artifact phenomenon. In particular, the characteristic effects of the present invention are as follows: (1) The avoidance of the artifact phenomenon is made possible without having to add special instruments and operations even under variable imaging conditions, that is, if the location of the region of interest to be imaged, the object to be checked, and the size of the imaging field of the detector are variable at each projection. (2) The exact geometric distortion correction table can be obtained by a simple method at every projection angles without having to redesign the whole or the part of the apparatus.

Briefly, according to the invention, the apparatus for cone-beam X-ray computed tomography operates to correct an image geometric distortion of the projection data, detect the location of the field boundary of the distortion-corrected projection data, generate the projection data of a certain width from the detected location of the view field boundary through the effect of the extrapolation, and then reconstruct a distribution of X-ray attenuation coefficients from the extrapolated projection data. To prepare the exact geometric distortion correction table, the apparatus operates to apply the conventional process of preparing a geometric distortion correction table to the hole chart projection images of all the projection angles for preparing the geometric distortion correction table of all the projection angles, check the continuity between the adjacent tables for checking the correction table for determining whether or not it is inexact, prepare a new table through the interpolation of the previous and the successive correction tables, if any, and replace the inexact table with the new table. These operations result in realizing the exact geometric distortion correction table for all the projection angles.

DESCRIPTION OF THE PREFERRED EMBODIMENTS

Figure 1:
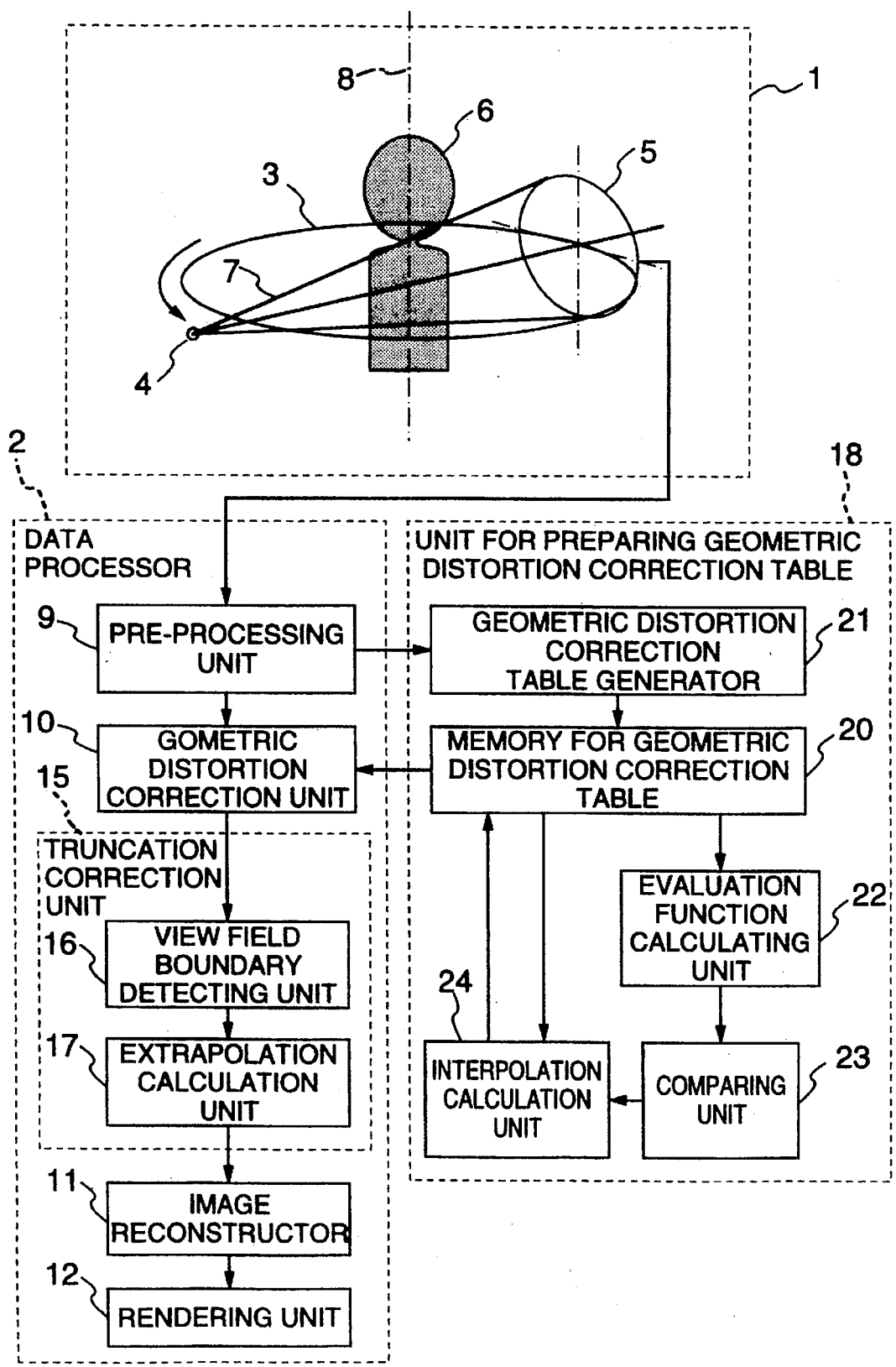
FIG. 1 is a block diagram showing an arrangement of an apparatus for cone-beam X-ray computed tomography according to an embodiment of the present invention.
Figure 2:
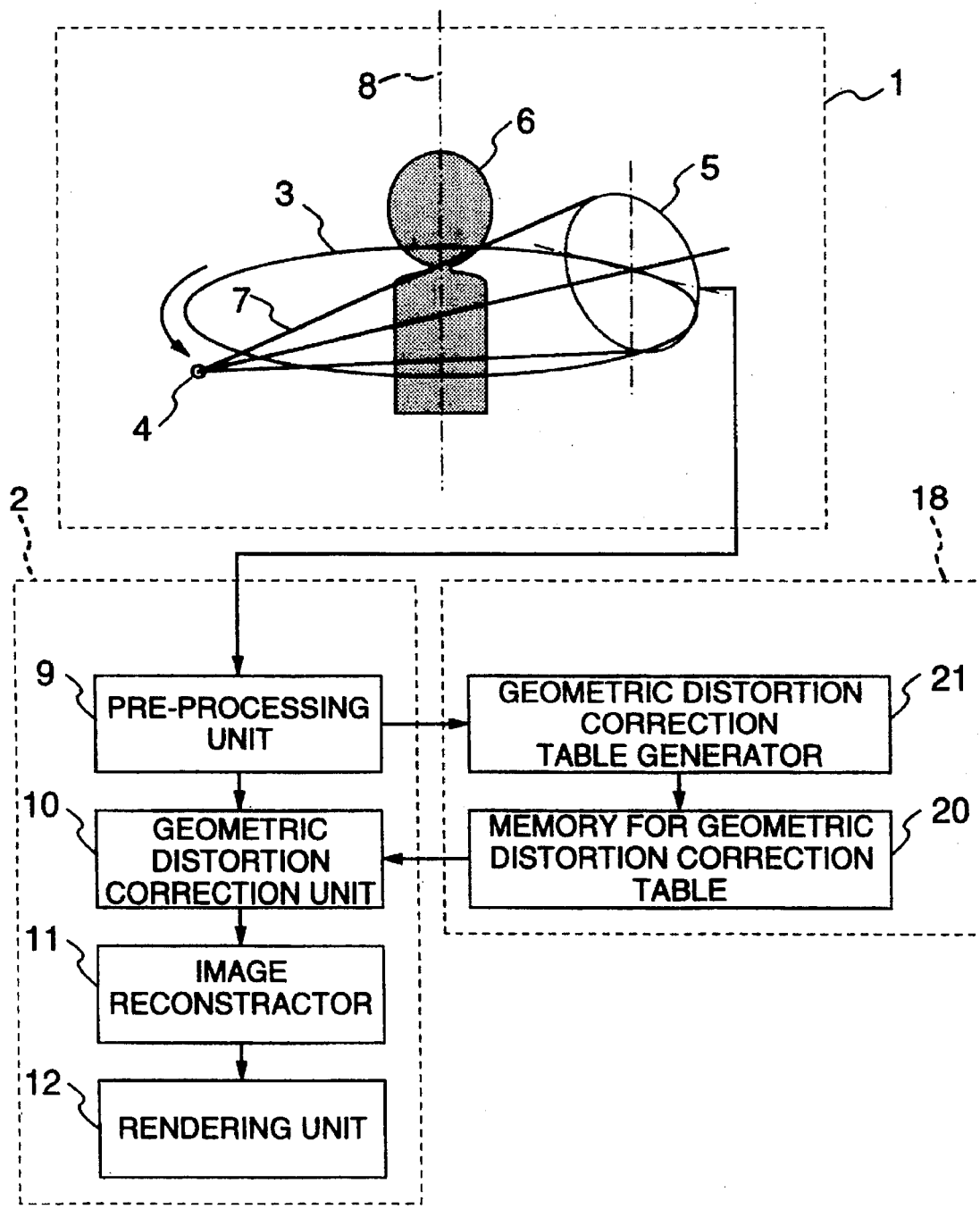
FIG. 2 is a block diagram showing an arrangement of the conventional apparatus for cone-beam X-ray computed tomography.
Figure 3:
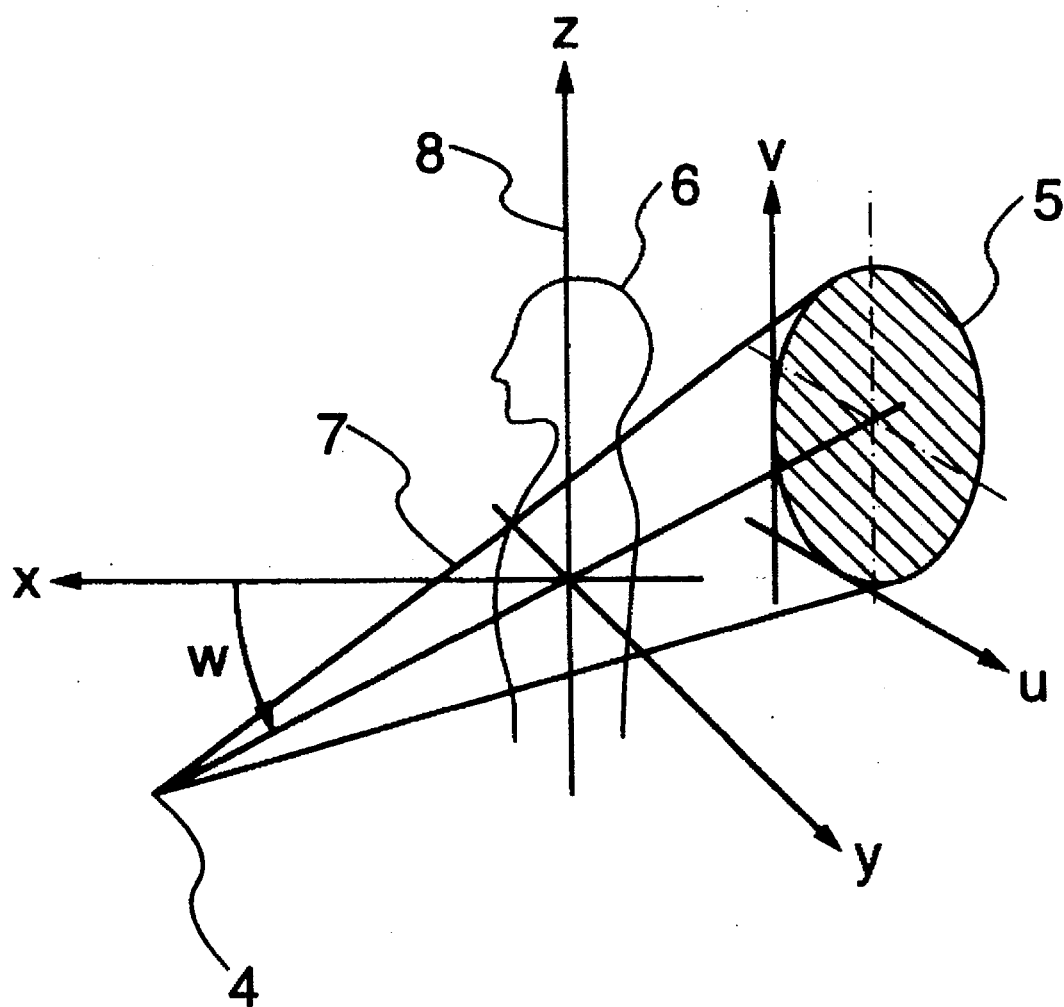
FIG. 3 is an explanatory view showing a geometric relation of a measuring unit provided in the apparatus for cone-beam X-ray computed tomography according to the invention.

Later, the description will be oriented to an embodiment of the invention with reference to the drawings. FIG. 1 is a block diagram showing an arrangement of an apparatus for cone-beam X-ray computed tomography. For further discussion, the geometric relation of a measuring system will be shown in FIG. 3. In FIG. 3, a three-dimensional coordinate system (x, y, z) is the Cartesian coordinates secured to the object, in which a z axis is a center axis 8 of rotation. An x-ray source 4 and a scanner 3 with a two-dimensional X-ray detector 5 (simply called a detector) installed thereon are rotated on the z axis. The angle of rotation of the scanner 3 is denoted by w. A two-dimensional coordinate system (u, v) is the Cartesian coordinates secured to the detector 5, in which a v axis is parallel to the z axis and a u axis is parallel to the tangent of the rotation. At first, like the prior art, the measured data obtained by imaging the object is pre-processed for converting it to the projection data in a pre-processing unit 9. The pre-processes contain a dark current bias correction, a correction for a non-uniform distribution of sensitivity of the detector, and a logarithm transformation. This projection data is saved in a first memory (not shown) and is represented by Pd(m, n, k). Assuming that m, n and k are an index for the u direction, an index for the v direction, and an index for the rotation angle w of the scanner 3, respectively, and $N_m$, $N_n$ and $N_k$ are a number of u-directional data pieces, a number of v-directional data pieces, and a number of projections, respectively, the possible ranges of m, n and k are $\{1, 2, \ldots, N_m\}$, $\{1, 2, \ldots, N_n\}$ and $\{1, 2, \ldots, N_k\}$, respectively.

Next, the image geometric distortion is corrected in a geometric distortion correction unit 10. The correction is executed on a geometric distortion correction table, the preparation of which will be described below. This distortion-corrected projection data is saved in a second memory (not shown), in which the data is represented as P(i, j, k). Assuming that i, j and k are an index for the u direction, an index for the v direction, and an index for an angle of rotation w of the scanner 3, respectively and N, Nj and Nk are a number of u-directional data pieces, a number of v-directional data pieces, and a number of projections, respectively, the possible ranges of i, j and k are $\{1, 2, \ldots, N_i\}$, $\{1, 2, \ldots, N_j\}$ and $\{1, 2, \ldots, N_k\}$, respectively. At a time, between the distortion-corrected projection data and the projection data before the correction, the relation of P(i, j, k)=Pd(M(i, j, k), N(i, j, k), k) is set up. M(i, j, k) and N(i, j, k) are functions about i, j and k derived according to how much the image is geometrically distorted. These functions do not normally yield integer values. Hence, P(i, j, k) are interpolated from Pd(M(i, j, k), N(i, j, k), k) through the effect of a technique such as a linear interpolation. Since the region located out of the view field of the detector 5 is determined on the projection data before correcting the distortion, if Pd(M(i, j, k), M(i, j, k), k) stays out of the view field, zero is substituted in P(i, j, k).

Next, upon the projection data obtained after correction of geometric distortion, a truncation correction for the status that the projection data is out of view field is performed in truncation correction unit 15. The truncation correction unit 15 includes view field boundary detecting unit 16 and extrapolation calculation unit 17. The truncation correction processing includes a processing (1) for detecting a view field boundary in the view field boundary detecting unit 16 and an extrapolation processing (2) in the extrapolation calculation unit 17.

At first, (1) detection of a view field boundary will be described. As mentioned above, after the image distortion is corrected, the form of the view field boundary of the detector 5 is variable according to each projection. Hence, the process of detecting the field boundary is executed for detecting the field boundary of the detector for each projection. Herein, the distortion-corrected projection data P(i, $j_0$, $k_0$) in which $\{i=1, 2, \ldots, N_i\}$ is assumed for any $j_0$ and $k_0$ is called a scan line. The field boundary is detected by scanning the distortion-corrected projection data P(i, j, k) at each scan line in the i direction. Based on a certain scan line, the view field boundary with a smaller value of i is called a left end, while the field boundary with a larger value of i is called a right end. To specify the left end of the field, as incrementing a value of i from 1, the scan line is being checked until a value other than zero is found on the scan line. If such a value is found, that is the left end of the view field on the scan line. If such a value is not found until $i=N_i$, it indicates that the overall scan line is out of the view field of the detector 5. If the left end is found, then, the right end of the view field on the scan line is detected. That is, as decrementing a value of i from $N_i$, the scan line is being checked until a value other than zero is found. If the overall scan line is not located out of the view field, the above-described operations are realized to detect the left and the right ends of the view field, that is, the view field boundary.

In some relation between the view field and the object 6, the projection data may have zero if the scan line stays within the view field of the detector. If a value of zero is used for indicating out of the field, in such a relation, the exact field boundary may not be detected. In that situation, the detected field boundary actually indicates the contour of the object. However, this detected field boundary may be assumed as a temporary field boundary for executing the subsequent extrapolation. In the foregoing description, zero is saved in portions out of the view field when correcting an image geometric distortion. In actual, however, any special value may be used if it is distinguishable from the projection value inside the view field. In the latter case, when extracting the field boundary, the scan line is being scanned until any value other than the value indicating the out of field is reached.

Figure 4:
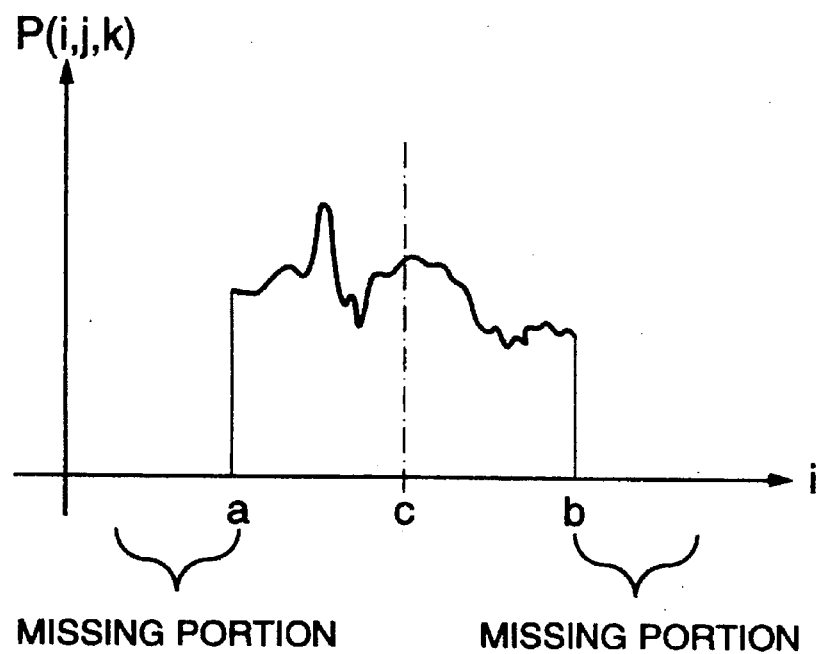
FIG. 4 is a view showing a profile of projection data with a truncated portion of an object to be imaged.

Next, (2) the extrapolation processing will be described. FIG. 4 shows a profile of one scan line of a typical projection data with a missing portion, because a portion of the object is out of the field of view. The left end of the field of the overall scan line found when detecting the field boundary is assumed to be i=a and the right end thereof is assumed to be i=b. If the overall scan line stays out of the field, no processing is executed for this scan line, and then the processing is transferred to the next scan line. c denotes a crosspoint between this scan line and a straight line formed by projecting the center axis of rotation x=y=0 on the uv plane or a point derived by the expression of c=(a+b)/2.

As shown in FIG. 4, the section [a, b] indicates the field. The projection data out of the field is missing. The projection data is discontinuously changed at the field ends of i=a, b.

The foregoing Feldkamp's cone-beam reconstructing operation is executed so that the Shepp-Logam function or its analogous correction filter is acted for the projection data. The correction filter serves to emphasize a high frequency component of the projection data, so that a spike-like peak appears on the field ends of the projection data, that is, at the points of i=a, b. The back projection of the filtered projection data results in bringing about a shading artifact on the reconstructed data. To avoid the artifact, the apparatus of this embodiment operates to do an extrapolating process in the portion out of view field for generating continuous projection data (1) continued with the projection data which is present in the view field at the field ends of i=a, b and projection data (2) taking zero at points separated by a certain width from the field ends of i=a, b. The filtering process executed in the cone-beam reconstructing operation is proceeded only in the i direction. Hence, this extrapolating process is just required to consider only the i-directional continuity. The later discussion concerns with only the i-directional extrapolation.

Figure 5:
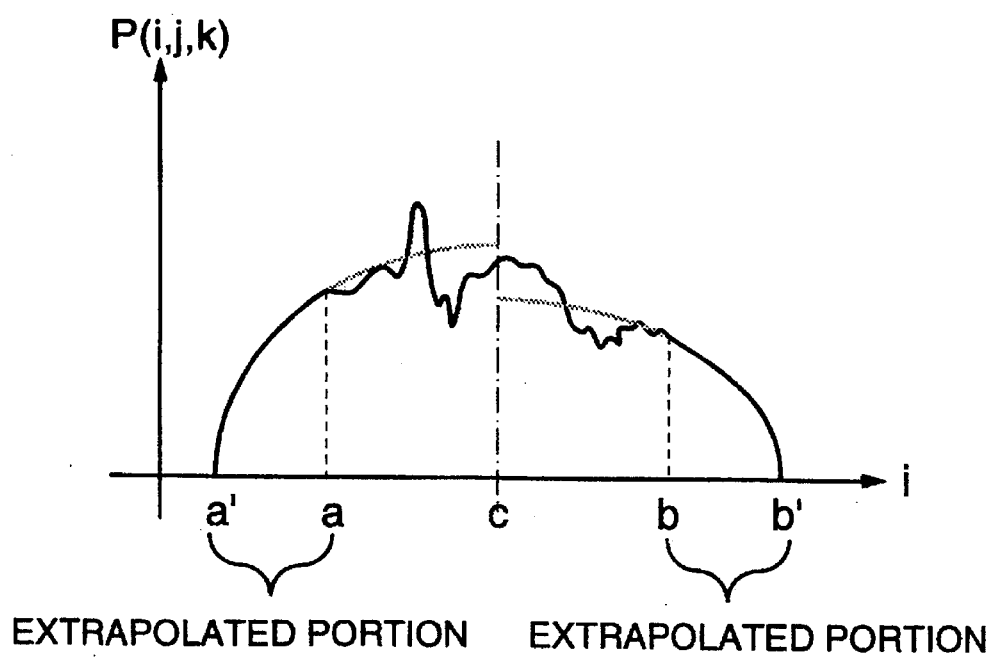
FIG. 5 is a view showing a profile of projection data extrapolated by the apparatus of the invention.
Figure 6:
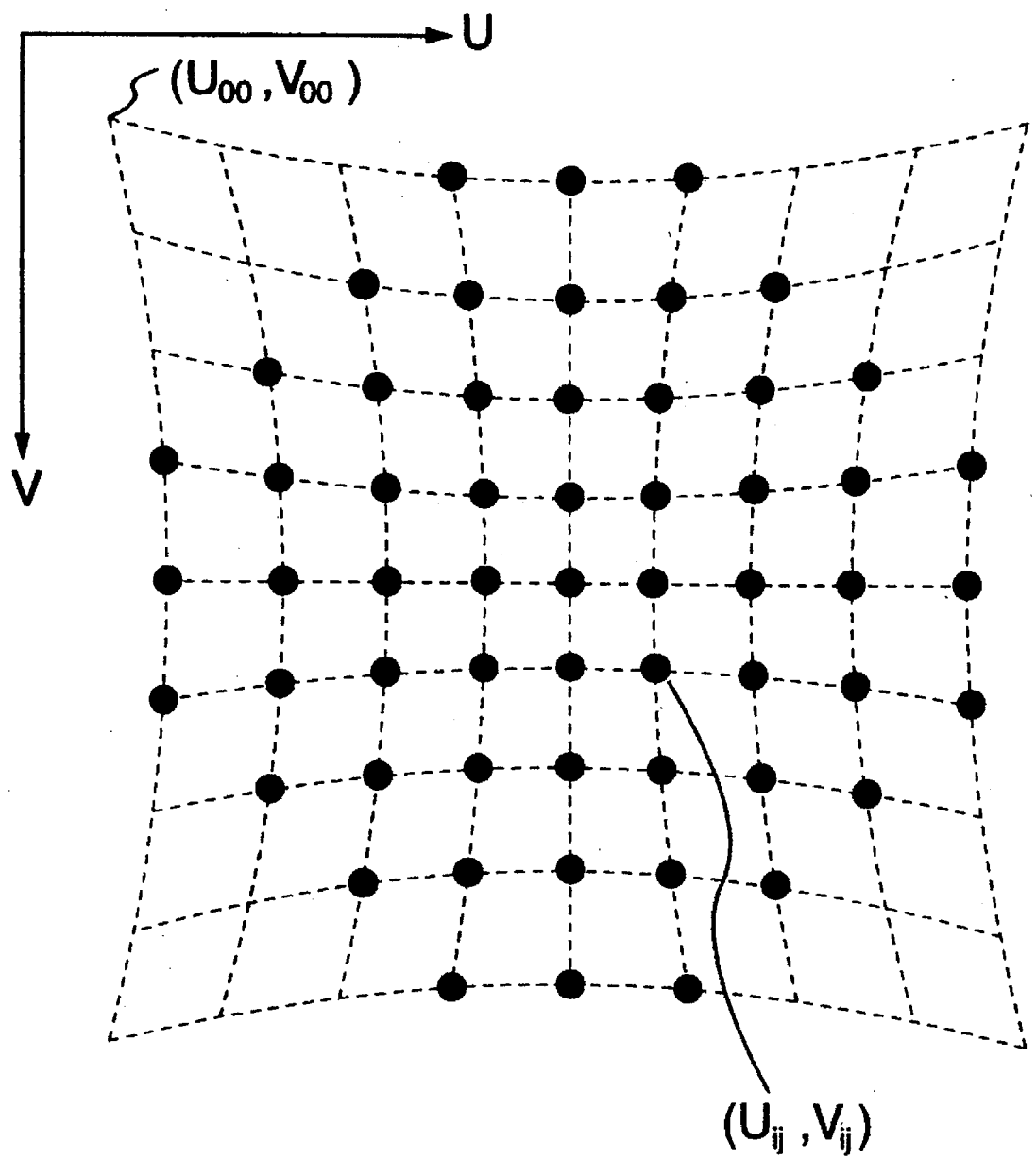
FIG. 6 is a view showing locations of pin hole images on a hole chart projection image with an image geometric distortion output by the prior art.
Figure 7:
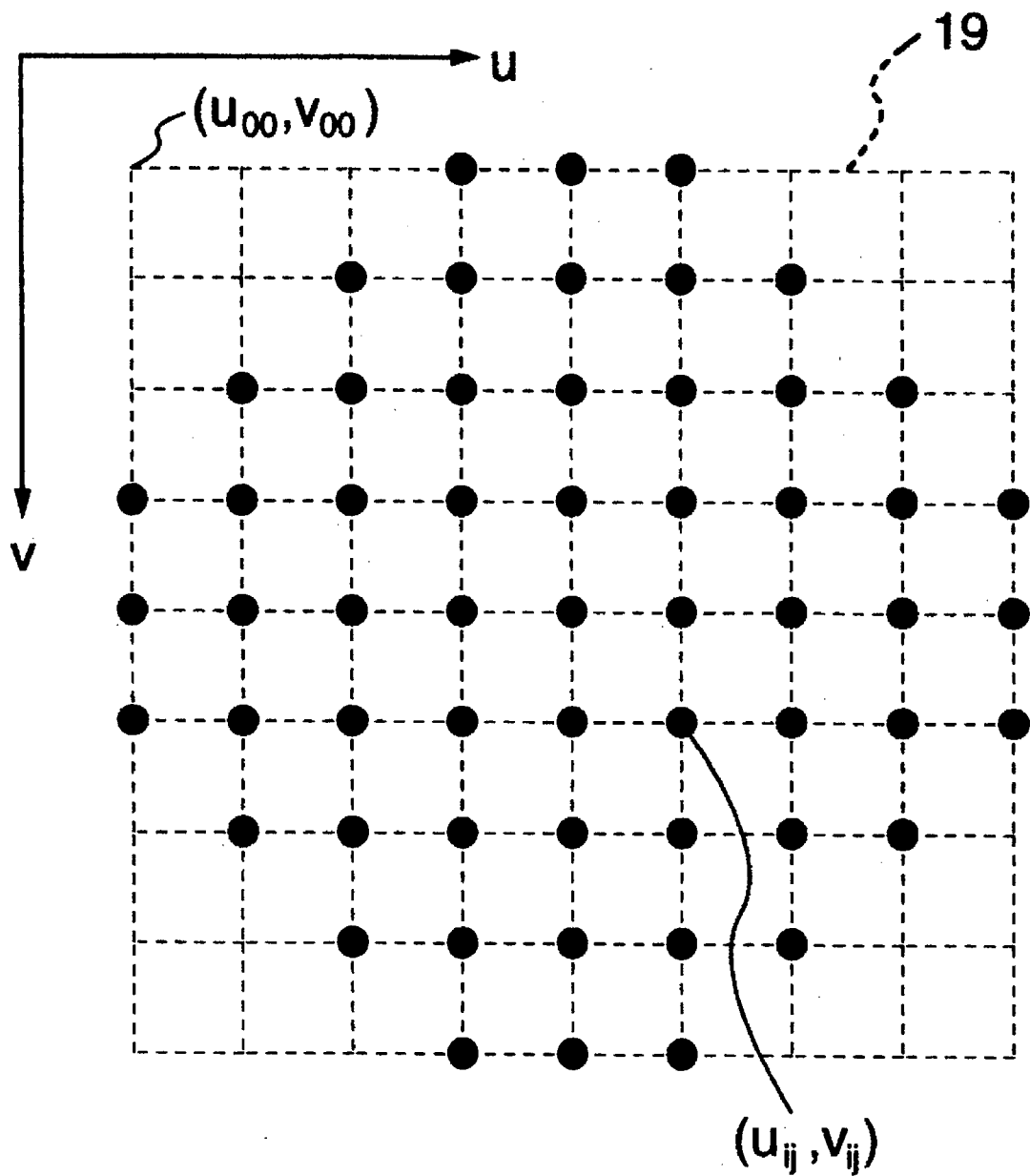
FIG. 7 is a view showing location of pin holes on a hole chart projection image used in the prior art.

Later, the description will be oriented to a concrete extrapolating method meeting the foregoing conditions of this embodiment. At first, the method for creating extrapolation data on the side of i<a is described. As shown in FIG. 5, the extrapolated curve is made to be (1) an ellipse with a straight line i=c and an i axis as its axes and pass through (2) a point (a, P(a, j, k)) and (3) a point (a', 0). If the extrapolating width is assumed as D, the value of a' is defined as a'=a−D. The ellipse meeting the condition (1) is represented by the expression (3);

$$\left(\frac{i-c}{A}\right)^2 + \left(\frac{P(i,j,k)}{B}\right)^2 = 1 \tag{3}$$

wherein A is a major axis and B is a minor axis.

The values of A and B are determined on the expression (4) so that these A and B meet the conditions (2) and (3).

$$A^2 = (a' - c)^2 \tag{4}$$

$$B^2 = P(a,j,k)^2 \frac{(a'-c)^2}{(a'-c)^2 - (a-c)^2}$$

In turn, the extrapolation of a section (a', a] is derived by the expression (5);

$$P(i,j,k) = P(a,j,k)\sqrt{\frac{(a'-c)^2 - (u-c)^2}{(a'-c)^2 - (a-c)^2}} \quad a' \leq u < a \tag{5}$$

On the other hand, about the section (b, b'], the variables of a and a' are replaced with b and b' (where b'=b+D). That is, the foregoing extrapolation will be summarized below. If on the projection plane of the detector the u axis is located in the direction of rotation of the scanner and the v axis is located in parallel to the center axis of rotation of the scanner, a projection value at the k-th projection location (u, v) is P(u, v, k), the boundary of the field detected about a certain value of v is (a(v), v) and (b(v), v) (where a(v)<b(v)). And, if the projection of the center axis of rotation is a straight line u=c and the certain width to be extrapolated is D, the projection data out of the view field is extrapolated according to the expression (6) in the region out of the view field u<a(v) and b(v)<u.

$$P(u,v,k) = \begin{cases} P(a(v),v,k)\sqrt{\dfrac{(a(v)-D-c)^2-(u-c)^2}{(a(v)-D-c)^2-(a(v)-c)^2}} & a(v)-D \leq u < a(v) \\[2ex] P(b(v),v,k)\sqrt{\dfrac{(b(v)+D-c)^2-(u-c)^2}{(b(v)+D-c)^2-(b(v)-c)^2}} & b(v) < u \leq b(v)+D \\[2ex] 0 & u < a(v)-D, b(v)+D < u \end{cases} \tag{6}$$

The foregoing pre-process, geometric distortion correction, and extrapolation may be executed at a batch after all the projection data is obtained or at each projection. The Feldkamp's cone-beam reconstructing operation, however, may perform a reconstructing operation for each projection. Hence, the method for performing the pre-process, the geometric distortion correction, and the extrapolation for each projection is superior in that the operations (the pre-processing, the geometric distortion correction, the extrapolation and the reconstructing operation) are done concurrently with imaging an object.

Further, the pre-process, the geometric distortion correction, the extrapolation and the reconstructing operation are executed for each scan line. Hence, these processes may be performed in that order at each scan line. This method is effective in reducing in size the necessary volume of the storage means for temporarily saving the extrapolated projection data. In place of doing these processes for each projection or scan line in turn, the units for doing these processes are multiplexed so that these processes may be done concurrently for a group of some projections or scan lines.

As set forth above, this method allows the values of a' and b' and the width of the extrapolated projection data to be optionally determined before imaging the object. This is advantageous in that fast calculations are made possible when doing a filtering process for the reconstructing operation. As mentioned above, the cone-beam reconstruction operation is executed to apply the Shepp-Logan function or its analogous correction filter to the projection data in the operating process. In general, this filtering process uses the fast Fourier transform for reducing an amount of calculations. As well known in the art, the fast Fourier transform displays the most excellent performance when the number of data pieces is a power of 2. For example, if the number of data pieces to be input is 480, the number is made to be 512 by padding the zero values before doing the fast Fourier transform.

On the contrary, if the number of data pieces is 513, for example, the number has to be increased to 1024. This results in extremely increasing the amount of calculations. For example, assume that the used extrapolating method is arranged to define the width of the extrapolated projection data based on the information about the contour of the object 6. In this case, the number of data pieces does not necessarily reach the most approximate number for the fast Fourier transform. This method may, hence, bring about increase of an amount of calculations. However, the foregoing extrapolating method according to the present invention allows the width of the extrapolated projection data to be set to a suitable value for the filtering process.

This is quite advantageous because the reconstructing operation done in the cone-beam X-ray computed tomography needs a massive amount of filtering processes. Of course, the foregoing extrapolation may use a higher degree function. The complexity of the function is determined on the required accuracy, the time of calculation, the cost taken in installing the calculating unit, and the cost taken in manufacturing the apparatus. Further, the cone-beam X-ray computed tomography apparatus may be arranged so that the view field of the detector 5 changes according to a selected one of imaging modes. However, the method of this invention may perform the same processing even if the imaging condition is changed.

Moreover, the method of the invention is not influenced by the location of the region of interest to be imaged and each feature of the object 6. This is quite advantageous in that the method may apply to various imaging conditions without changing the apparatus scale and the amount of calculations. According to the foregoing embodiment, the artifact phenomenon on the reconstruction data may be avoided without calculating a large amount of extra information and load in reconstructing the image.

In turn, the description will be oriented to the embodiment of the invention for overcoming the second shortcoming, that is, the shortcoming about a method for preparing the geometric distortion correction table used in the cone-beam X-ray computed tomography. At first, a hole chart 19 is fixed to the front of the detector 5 for taking a hole chart projection image. On the projection image, the geometric distortion table is prepared. The projection image obtained by measuring the object is represented by Pd(U, V, k), wherein k is a location (angle of rotation) of a scanner as mentioned above and takes a value of 1, 2, . . . , $N_k$ ($N_k$ is the number of all the projections), and U and V are coordinates on an original image. U is in parallel to the rotating direction of the scanner and takes a value of 1, 2, . . . , $N_m$. V is in parallel to the center axis of rotation of the scanner and takes a value of 1, 2, . . . , $N_n$ ($N_m$ or $N_n$ is a number of matrixes of the detector. The geometric distortion corrected projection data used for reconstructing a three-dimensional image is represented by P(u, v, k), wherein u and v are coordinates on the projection data. u is in parallel to the rotating direction of the scanner and takes a value of 1, 2, . . . , $N_i$. v is in parallel to the center axis of rotation of the scanner and takes a value of 1, 2, . . . , $N_j$. ($N_i$ or $N_j$ is a number of matrixes of the detector, and $N_m=N_i$ and $N_n=N_j$ are commonly held.) Between them above mentioned, the relation of P(u, v, k)=Pd(U(u, v, k), V(u, v, k), k) is held. The functions U(u, v, k) and V(u, v, k) represent the image geometric distortion. The functions are tabulated with u, v and k as indexes so that they may be used for correcting the image geometric distortion. This is the geometric distortion correction table used in the apparatus for the cone-beam X-ray computed tomography. Of course, the actual values of k, u, v, U and V are integers. Hence, the geometric distortion corrected projection data P(u, v, k) for all the points of (u, v, k) is derived according to the expression (7) of the four-point Lagrangian interpolation, where U and V are maximum integers that do not surpass U(u, v, k) and V(u, v, k). This is an expansion of the geometric distortion correction mentioned as the prior art about a projection angle (corresponding to an index) k $$P(u,v,k) = (1 - U(u,v,k) + U)(1 - V(u,v,k) + V) \cdot \quad (7)$$
$$Pd(U,V,K) +$$
$$(U(u,v,k) - U)(1 - V(u,v,k) + V) \cdot$$
$$Pd(U+1,V,k) +$$
$$(1 - U(u,v,k) + U)(V(u,v,k) - V) \cdot$$
$$Pd(U,V+1,k) +$$
$$(U(u,v,k) - U)(V(u,v,k) - V) \cdot$$
$$Pd(U+1,V+1,k)$$

Figure 8:
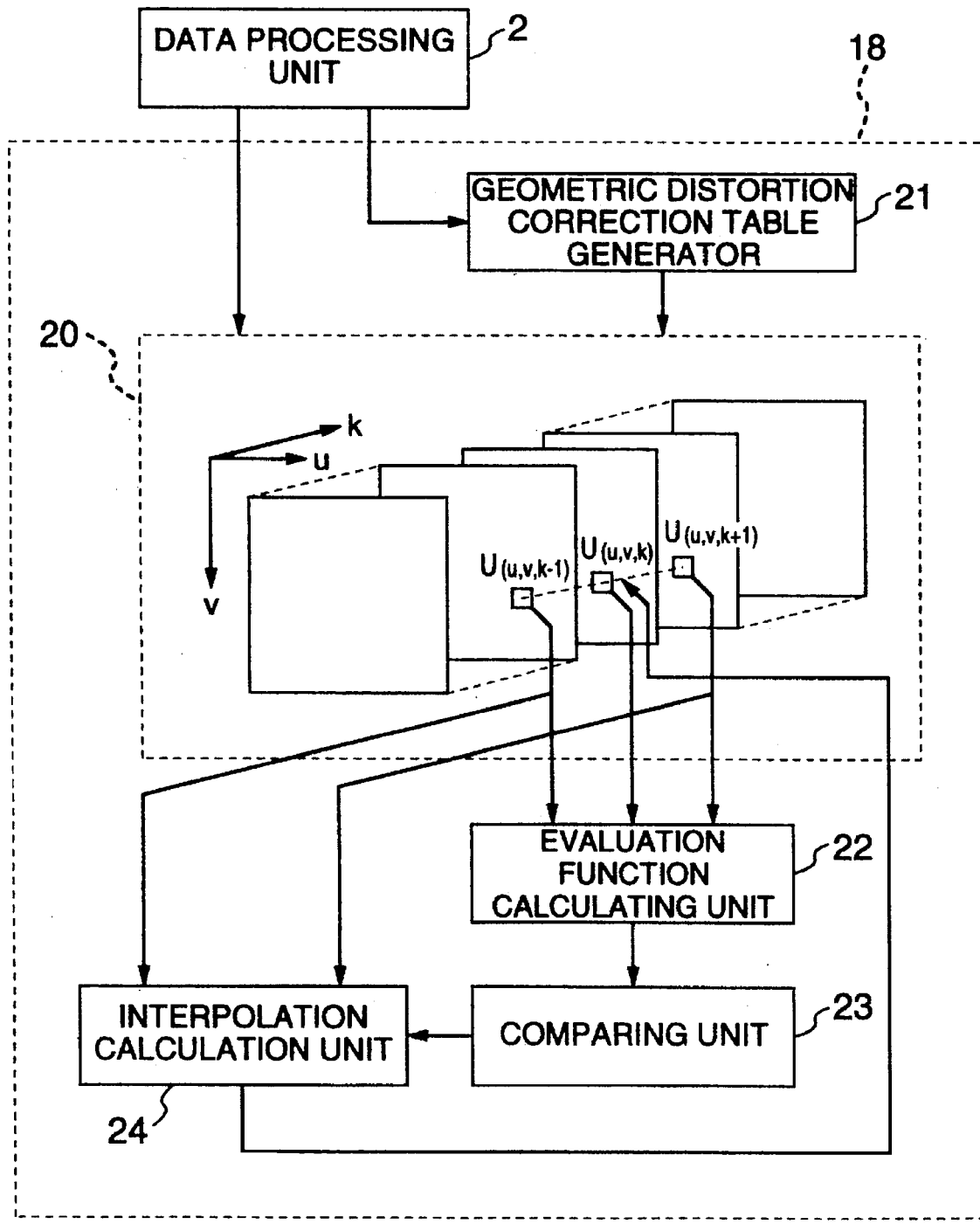
FIG. 8 is a view showing a detailed arrangement of a unit for preparing a geometric distortion correction table according to the present invention.

Next, the description will be oriented to the method for preparing a geometric distortion correction table according to an embodiment of the present invention. FIG. 8 shows the unit 18 for preparing a geometric distortion correction table in detail. At first, a geometric distortion correction table generator 21 operates to apply the conventional method for generating the geometric distortion correction table to all the projections and generates the geometric distortion correction table from the hole chart projection image. As is apparent from the foregoing cause, the geometric distortion correction table does not necessarily have exact data about all the projections. Then, in a unit 22 for calculating an evaluation function, the evaluation function is calculated for evaluating whether or not the correction table of each projection is exactly prepared. The resulting function value is compared with a specific threshold value in a comparing unit 23. If the former is equal to or greater than the latter, it indicates that the correction table is not exactly prepared. If the correction table is determined to be inexact, an interpolation calculation unit 24 operates to replace the inexact table with a new correction table obtained by doing the interpolating calculation using the geometric distortion correction tables. By repeating these operations, the exact geometric distortion correction tables are prepared for all the projections and then saved in a memory 20 for saving a geometric distortion correction table.

Next, the contents of the process will be described in more detail.

If the correction table is exactly prepared, it is assumed that the correction table U(u, v, k) and V(u, v, k) are continuously changed about u, v and k. If an adverse effect such as noise inhibits to prepare the exact correction table about a certain projection, U(u, v, k) and V(u, v, k) are discontinuously changed particularly in the k direction. Using this property, the k-directional continuity of the correction table is checked for determining whether or not the correction table is exactly prepared. In this determination, the function for evaluating the correction table about a projection k is represented by val(k). After the function val(k) is calculated for all the projections, it is determined that the geometric distortion correction table is correctly prepared for a projection which does not surpass a threshold value.

The expression (8) indicates the method for calculating the evaluation function val(k). This function to be indicated below operates to evaluate the U-directional and the V-directional correction tables respectively. Hence, the function is represented by valU(k) and valV(k). If k=1 or k=$N_k$, the function calculation needs a projection corresponding to k=0 or k=$N_k$+1. In actual, such a projection does not exist. In place, the projection corresponding to k=$N_k$ or k=1 is used for the function calculation. This replacement is valid since the projection is returned to an original position after one turn.

$$valU(k) = \sum_{v=1}^{N_j} \sum_{u=1}^{N_i} \sum_{l=-1}^{+1} (U(u,v,k+l) - \overline{U}(u,v,k))^2 \quad (8)$$

$$valV(k) = \sum_{v=1}^{N_j} \sum_{u=1}^{N_i} \sum_{l=-1}^{+1} (V(u,v,k+l) - \overline{V}(u,v,k))^2$$

where $$\overline{U}(u,v,k) = \frac{1}{3} \sum_{l=-1}^{+1} U(u,v,k+l)$$

$$\overline{V}(u,v,k) = \frac{1}{3} \sum_{l=-1}^{+1} V(u,v,k+l)$$

Figure 9:
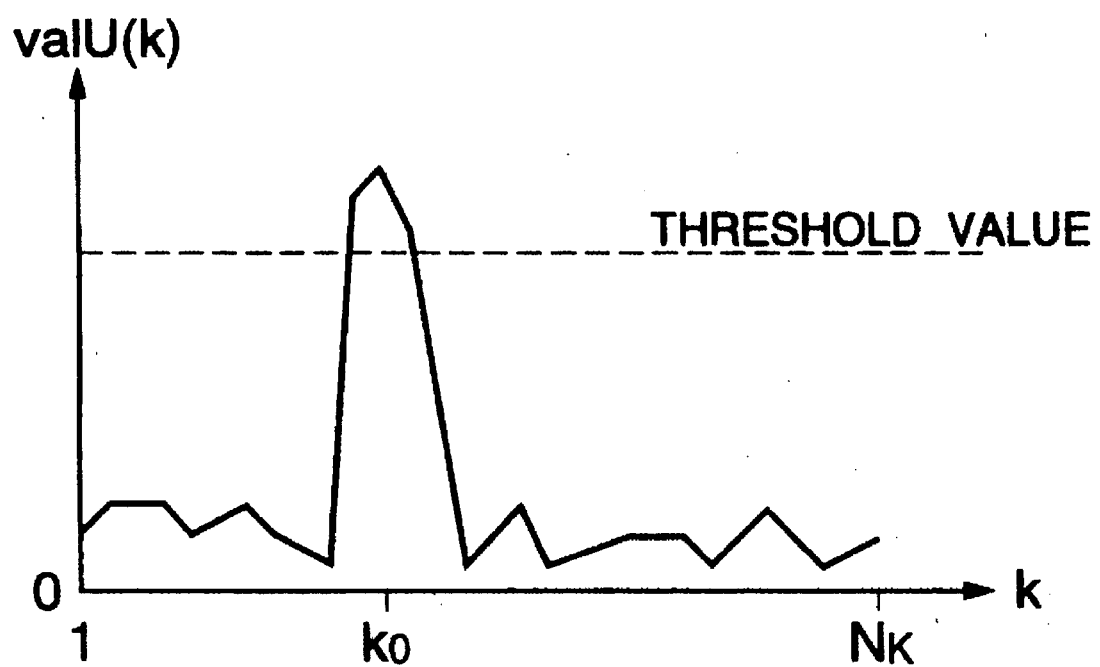
FIG. 9 is a view showing a change of an evaluation function valU(a) used in the present invention.

The expression (8) indicates the variances of the correction table values are dispersed among a subject projection k, the previous projection (k−1) and the subsequent projection (k+1) are calculated and then these variances are summed up about all the pixels of the projection k. Since the correction tables are continuously changed between the projections, the functions valU(k) and valV(k) indicate a great value if a discontinuous change appears therebetween. For calculating the variances, it is possible to use four or more projections. In this method, such a great value appears in the function valU($k_0$) (or valV($k_0$)) for the subject inexact correction table as well as the functions for the adjacent tables such as valU($k_0$−1) and valU($k_0$+1) (valV($k_0$−1) and valV($k_0$+1)). If the function valU(k)(valV(k)) surpasses a threshold value about the continuous k=$k_0$, $k_0$+1, ..., $k_0$+n, it indicates that the exact correction table is not prepared in the projections except the first one $k_0$ and the last one $k_0$+1, concretely, the projections k=$k_0$+1, ..., $k_0$+n−1. FIG. 9 is a graph showing the function valU(k) is plotted about k. This case indicates that the correction table of k=$k_0$ is not exact. In any case, it is presumed that the number of projections determined to be inexact by the foregoing checking method is far smaller than the number of all the projections. Hence, an operator may individually check the correction tables automatically determined to be inexact and determine if the correction tables are exact by himself.

Next, based on the foregoing check, the correction table determined to be inexact are removed and then replaced with a new table generated by interpolating the previous and the subsequent correction tables. For example, it is assumed that the correction table at the projection $k_0$ is determined to be inexact and the exact correction tables located most closely in the k direction are those at the projections $k_1$ and $k_2$ ($k_1$<$k_0$<$k_2$). The correction table U (u, v, $k_0$) and V(u, v, $k_0$) at the projection $k_0$ is derived by the following expression (9).

$$U(u,v,k_0) = \frac{k_2 - k_0}{k_2 - k_1} \cdot U(u,v,k_1) + \frac{k_0 - k_1}{k_2 - k_1} \cdot U(u,v,k_2) \quad (9)$$

$$V(u,v,k_0) = \frac{k_2 - k_0}{k_2 - k_1} \cdot V(u,v,k_1) + \frac{k_0 - k_1}{k_2 - k_1} \cdot V(u,v,k_2)$$

For interpolating the correction tables, a higher degree interpolating operation may be used. Since, in essence, the correction table is continuously changed in the projecting direction as mentioned above, the generation of the correction table through the effect of the interpolation is quite valid. According to the foregoing embodiment, therefore, a simple method allows the exact geometric distortion correction tables to be prepared for all the projection angles without having to redesign all or part of the apparatus.

The expression (8) for calculating the evaluation function valU(k) and valV(k) is generalized by the expression (10) for calculating the evaluation function using p projections. In the case of $$valU(k) = \sum_{v=1}^{N_j} \sum_{u=1}^{N_i} \sum_{l=-p}^{p} (U(u,v,k+l) - \overline{U}(u,v,k))^2 \quad (10)$$

$$valV(k) = \sum_{v=1}^{N_j} \sum_{u=1}^{N_i} \sum_{l=-p}^{p} (V(u,v,k+l) - \overline{V}(u,v,k))^2$$

where $$\overline{U}(u,v,k) = \frac{1}{2p+1} \sum_{l=-p}^{p} U(u,v,k+l)$$

$$\overline{V}(u,v,k) = \frac{1}{2p+1} \sum_{l=-p}^{p} V(u,v,k+l)$$

In the case of p=1 at the expression (10), the expression (8) is obtained. If the evaluation function (the expression (10)) of the projections in the serial direction (k=$k_0$, $k_0$+1, ..., $k_0$+n; k is integer) has a greater than a specific threshold value, the prepared correction table of the projection k=$k_0$+1, ..., $k_0$+n−1 is deleted from the memory for saving (memorizing) the correction table, the correction table of the projection in k=$k_0$+1, ..., $k_0$+n−1 is derived by interpolations of prepared correction table in $k_0$ direction and ($k_0$+n) direction and then the correction table calculated by the interpolation is saved (memorized) in the memory. The interpolations are executed for deriving the correction table U(u, v, k) and V(u, v, k) which are deleted from the memory (where k=$k_0$+1, ..., $k_0$+n−1, $k_1$<$k_0$+1, $k_0$+n−1<$k_2$; k, $k_1$, $k_2$ are integer). The interpolations are calculated according to the expression of;

$$U(u,v,k) = \frac{k_2 - k}{k_2 - k_1} \cdot U(u,v,k_1) + \frac{k - k_1}{k_2 - k_1} \cdot U(u,v,k_2) \quad (11)$$

$$V(u,v,k) = \frac{k_2 - k}{k_2 - k_1} \cdot V(u,v,k_1) + \frac{k - k_1}{k_2 - k_1} \cdot V(u,v,k_2)$$

The prepared correction table U(u, v, $k_1$), V(u, v, $k_1$) is located immediately before the deleted correction table, and the prepared correction table U(u, v, $k_2$), and V(u, v, $k_2$) is located immediately after the deleted correction table.

What is claimed is:

1. A method for cone-beam X-ray computed tomography in which a scanner mounting an X-ray source for applying a cone-beam X ray and a two-dimensional X-ray detector for detecting an X-ray is rotated around an object to measure omnidirectional projection data around said object and a distribution of X-ray attenuation coefficients of said object is reconstructed, comprising the steps of:

correcting an image geometric distortion of said projection data;

detecting a view field boundary of said two-dimensional X-ray detector from said projection data whose geometric distortion is corrected;

extrapolating projection data of a predetermined width from said view field boundary detected in the step of detecting a view field and boundary; and reconstructing said distribution of X-ray attenuation coefficients of said object from said projection data extrapolated in the step of extrapolating projection data.

2. A method for cone-beam X-ray computed tomography as claimed in claim 1, wherein the step of correcting comprises a step of setting, a value indicating being out of view field to a region whose geometric distortion is corrected in said projection data before the image geometric distortion is corrected, said region located out of the view field of said two-dimensional X-ray detector.

3. A method for cone-beam X-ray computed tomography as claimed in claim 2, wherein said value to be set is zero.

4. A method for cone-beam X-ray computed tomography as claimed in claim 2, wherein the step of detecting the view field boundary comprises a step of sequentially scanning said distortion-corrected projection data in parallel to the tangent of the rotation of said scanner, and if a point has any value other than the value indicating out of the view field, detecting the point as said boundary of the view field.

5. A method for cone-beam X-ray computed tomography as claimed in any one of claims 1 to 4, wherein the step of extrapolating comprises a step of, in said projection data whose boundary of the view field is detected, extrapolating the projection data of only said predetermined width from said detected view field boundary to said region of out of the view field in parallel to the rotation of said scanner.

6. A method for cone-beam X-ray computed tomography as claimed in claim 5, wherein the step of extrapolating comprises a step of extrapolating so that said projection data in the region located out of the view field is concatenated with said projection data located within said view field and forms such a part of an arc of an ellipse as taking zero at a point spaced by a certain width from said view field boundary.

7. A method for cone-beam X-ray computed tomography as claimed in claim 5, wherein the step of extrapolating comprises a step of, if the rotating direction of said scanner is set to a u axis and the center axis of rotation of said scanner is set to a v axis on a projection plane of said two-dimensional X-ray detector, assuming that a projection value at the k-th projection location (u, v) is P(u, v, k), the location of said view field boundary detected about a certain value of v is (a(v), v) and (b(v), v) (wherein a(v)<b(v)), the projection of the center axis of rotation is a straight line u=c, and the certain width to be extrapolated is D, in the region located out of the view field of u<a(v) and b(v)<u, extrapolating the projection data located out of the view field according to the expression of;

extrapolating means for generating said projection data of a predetermined width from said view field boundary location detected by said detecting means; and means for reconstructing the distribution of X-ray attenuation coefficients of said object from said projection data extrapolated in said extrapolating means.

9. An apparatus for cone-beam X-ray computed tomography as claimed in claim 8, wherein said means for correcting an image geometric distortion of said projection data comprises means for setting a value indicating the out of view field to the distortion-corrected region corresponding to the region located out of the view field of said two-dimensional X-ray detector.

10. An apparatus for cone-beam X-ray computed tomography as claimed in claim 9, wherein said value to be set is zero.

11. An apparatus for cone-beam X-ray computed tomography as claimed in claim 9, wherein said means for detecting a location of said view field boundary comprises means for sequentially scanning said projection data in parallel to the rotating direction of said scanner and detecting as the view field boundary points where any value other than the value indicating the out of view field appears.

12. An apparatus for cone-beam X-ray computed tomography as claimed in any one of claims 9 to 11, wherein said extrapolating means comprises means for extrapolating said projection data of said predetermined of said detected view field boundary to said region located out of the view field in parallel to the rotating direction of said scanner in said projection data whose view field boundary is detected.

13. An apparatus for cone-beam X-ray computed tomography as claimed in claim 12, wherein said extrapolating means comprises means for extrapolating the projection data so that said projection data in the region located out of the view field is concatenated with said projection data located within said view field and forms such a part of an arc of an ellipse as assuming zero at a point spaced by a certain width from said view field boundary.

14. An apparatus for cone-beam X-ray computed tomography as claimed in claim 12, wherein if the rotating $$P(u,v,k) = \begin{cases} P(a(v),v,k)\sqrt{\dfrac{(a(v)-D-c)^2-(u-c)^2}{(a(v)-D-c)^2-(a(v)-c)^2}} & a(v)-D \leq u < a(v) \\ P(b(v),v,k)\sqrt{\dfrac{(b(v)+D-c)^2-(u-c)^2}{(b(v)+D-c)^2-(b(v)-c)^2}} & b(v) < u \leq b(v)+D \\ 0 & u < a(v)-D, b(v)+D < u \end{cases}$$

8. An apparatus for cone-beam X-ray computed tomography having a scanner mounting an X-ray source for applying a cone-beam X ray and a two-dimensional X-ray detector for detecting an X-ray, means for rotating said scanner around an object, and means for measuring omnidirectional projection data around said object, said apparatus serving to reconstruct a distribution of X-ray attenuation coefficients of said object based on said projection data, comprising:

correcting means for correcting an image geometric distortion of said projection data;

detecting means for detecting a location of a view field boundary of said detector of said projection data whose geometric distortion is corrected by said correcting means;

direction of said scanner is set to a u axis and the center axis of rotation of said scanner is set to a v axis on a projection plane of said two-dimensional X-ray detector, assuming that a projection value at the k-th projection location (u, v) is P(u, v, k), the location of said view field boundary detected about a certain value of v is (a(v), v) and (b(v), v) (a(v)<b(v)), the projection of the center axis of rotation is a straight line u=c, and the certain width to be extrapolated is D, in the region located out of the view field of u<a(v) and b(v)<u, said extrapolating means comprises means for extrapolating said projection data located out of the view field according to the expression of;

$$P(u,v,k) = \begin{cases} P(a(v),v,k)\sqrt{\dfrac{(a(v)-D-c)^2-(u-c)^2}{(a(v)-D-c)^2-(a(v)-c)^2}} & a(v)-D \leq u < a(v) \\ P(b(v),v,k)\sqrt{\dfrac{(b(v)+D-c)^2-(u-c)^2}{(b(v)+D-c)^2-(b(v)-c)^2}} & b(v) < u \leq b(v)+D \\ 0 & u < a(v)-D, b(v)+D < u \end{cases}$$

15. A method for cone-beam X-ray computed tomography in which a scanner mounting an X-ray source for applying a cone-beam X ray and a two-dimensional X-ray detector for detecting an X-ray is rotated around an object to measure omnidirectional projection data around said object, an image geometric distortion of said projection data is corrected by referring to a geometric distortion correction table, and a distribution of X-ray attenuation coefficients of said object is reconstructed by using said distortion-corrected projection data comprising the steps of:

preparing said correction table and storing said table in means for saving a correction table;

calculating an evaluation function for evaluating continuity of said prepared correction table between the previous and the subsequent projections of each subject projection on which said projection data is obtained;

deleting said prepared correction table that is not continuously changed between said previous and subsequent projections from said means for saving a correction table, replacing said correction table that is not continuously changed with a new correction table interpolated from said prepared correction tables of the previous and the subsequent projections, and saving said new correction table in said means for saving a correction table; and reconstructing the distribution of X-ray attenuations of said object.

16. A method for cone-beam X-ray computed tomography as claimed in claim 15, wherein if on the plane of said two-dimensional X-ray detector for detecting said projection data a u axis is set to the rotating direction of said scanner, a v axis is set in parallel to the center axis of rotation of said scanner, and said prepared correction table of said k-directional projection is represented by U(u, v, k) and V(u, v, k) (k=1, 2, ..., $N_k$, u=1, 2, ..., $N_i$, v=1, 2, ..., N), said evaluation function is operated to calculate a correlation between said k-directional prepared correction tables in the step of calculating the evaluation function.

17. A method for cone-beam X-ray computed tomography as claimed in claim 15, wherein the step of calculating an evaluation function comprises a step of obtaining if k is any natural number, valU(u, v, k) and valV(u, v, k) (where if k+l is overflown out of the range of k=1, 2, ..., $N_k$ during the calculation, the tail is circulated to the head of k) as be said evaluation function according to the expression of;

$$valU(k) = \sum_{v=1}^{N_j} \sum_{u=1}^{N_i} \sum_{l=-p}^{p} (U(u,v,k+l) - \overline{U}(u,v,k))^2$$

$$valV(k) = \sum_{v=1}^{N_j} \sum_{u=1}^{N_i} \sum_{l=-p}^{p} (V(u,v,k+l) - \overline{V}(u,v,k))^2$$

where

-continued $$\overline{U}(u,v,k) = \dfrac{1}{2p+1} \sum_{l=-p}^{p} U(u,v,k+l)$$

$$\overline{V}(u,v,k) = \dfrac{1}{2p+1} \sum_{l=-p}^{p} V(u,v,k+l).$$

18. A method for cone-beam X-ray computed tomography as claimed in claim 15, wherein if on the plane of said two-dimensional X-ray detector for detecting said projection data a u axis is set to the rotating direction of said scanner, a v axis is set in parallel to the center axis of rotation of said scanner, and said prepared correction table of said k-directional projection is represented by U(u, v, k) and V(u, v, k) (k=1, 2, ..., $N_k$, u=1, 2, ..., $N_i$, v=1, 2, ..., N), and said evaluation function is operated to calculate a correlation between said k-directional prepared correction tables in the step of calculating said evaluation function, and wherein said prepared correction table in which the values of said evaluation function has a value meeting the specific conditions is determined to be the correction table that is not continuously changed.

19. A method for cone-beam X-ray computed tomography as claimed in claim 15, wherein the step of calculating an evacuation function comprises a step of obtaining if k is any natural number, valU(u, v, k) and valV(u, v, k) (where if k+l is overflown out of the range of k=1, 2, ..., $N_k$ during the calculation, the tail is circulated to the head of k) as be said evaluation function according to the expression of:

$$valU(k) = \sum_{v=1}^{N_j} \sum_{u=1}^{N_i} \sum_{l=-p}^{p} (\overline{U}(u,v,k+l) - \overline{U}(u,v,k))^2$$

$$valV(k) = \sum_{v=1}^{N_j} \sum_{u=1}^{N_i} \sum_{l=-p}^{p} (\overline{V}(u,v,k+l) - \overline{V}(u,v,k))^2$$

where $$\overline{U}(u,v,k) = \dfrac{1}{2p+1} \sum_{l=-p}^{p} U(u,v,k+l)$$

$$\overline{V}(u,v,k) = \dfrac{1}{2p+1} \sum_{l=-p}^{p} V(u,v,k+l),$$

and wherein said prepared correction table in which said evaluation function has a greater value than a specific threshold value is determined to be said correction table that is not continuously changed.

20. A method for cone-beam X-ray computed tomography as claimed in claim 15, wherein the step of calculating an evacuation function comprises a step of obtaining if k is any natural number, valU(u, v, k) and valV(u, v, k) (where if k+l is overflown out of the range of k=1, 2, ..., $N_k$ during the calculation, the tail is circulated to the head of k) as be said evaluation function according to the expression of:

$$valU(k) = \sum_{v=1}^{N_j} \sum_{u=1}^{N_i} \sum_{l=-p}^{p} (\overline{U}(u,v,k+l) - \overline{U}(u,v,k))^2$$

$$valV(k) = \sum_{v=1}^{N_j} \sum_{u=1}^{N_i} \sum_{l=-p}^{p} (\overline{V}(u,v,k+l) - \overline{V}(u,v,k))^2$$

where $$\overline{U}(u,v,k) = \frac{1}{2p+1} \sum_{l=-p}^{p} U(u,v,k+l)$$

$$\overline{V}(u,v,k) = \frac{1}{2p+1} \sum_{l=-p}^{p} V(u,v,k+l),$$

and wherein if said evaluation function has a greater value than a specific threshold value of said projections in the serial direction ($k=k_0$, $k_0+1$, ..., $k_0+n$), said prepared correction table of said projection in the direction of $k=k_0+1$, ..., $k_0+n-1$ is deleted from said means for saving correction table, the correction table of said projection in the $k=k_0+1$, ..., $k=k_0+n-1$ is derived by doing the interpolation of said prepared correction table in said $k_0$ and ($k_0\pm n$) directions and then is saved in said means for saving correction table.

21. A method for cone-beam X-ray computed tomography as claimed in claim 20, wherein said interpolation is executed for deriving said prepared correction table U(u, v, k) and V(u, v, k) (where $k=k_0+1$, ..., $k_0+n-1$, $k_1<k_0+1$, $k_0+n-1<k_2$) deleted from said means for saving correction table from said prepared correction table U(u, v, $k_1$) and V(u, v, $k_1$) immediately before said deleted correction table in said projecting direction and said prepared correction table U(u, v, $k_2$) and V(u, v, $k_2$) immediately after said deleted correction table in said projecting direction according to the expression of;

$$U(u,v,k) = \frac{k_2-k}{k_2-k_1} \cdot U(u,v,k_1) + \frac{k-k_1}{k_2-k_1} \cdot U(u,v,k_2)$$

$$V(u,v,k) = \frac{k_2-k}{k_2-k_1} \cdot V(u,v,k_1) + \frac{k-k_1}{k_2-k_1} \cdot V(u,v,k_2).$$

22. An apparatus for cone-beam X-ray computed tomography having a scanner mounting an x-ray source for applying a cone-beam X ray and a two-dimensional X-ray detector for detecting an X-ray, means for rotating said scanner around an object, means for measuring omnidirectional projection data around said object, means for preparing a correction table on which an image geometric distortion of said projection data is corrected, and means for correcting an image geometric distortion of said projection data by referring to said correction table, for reconstructing a distribution of X-ray attenuation coefficients of said object on said distortion-corrected projection data, comprising:

means for preparing said correction table having;

means for preparing said correction table of each projection for obtaining said projection data in advance;

evaluating means for calculating an evaluation function for evaluating continuity of said correction tables between the previous and the subsequent projections of a subject projection for obtaining said projection data, and comparing the value of the calculated evaluation function with a predetermined threshold value for evaluating said prepared correction table;

interpolating means for deriving said prepared correction table that is not continuously changed between said previous and subsequent projections from said prepared correction tables for said previous and subsequent projections through the effect of the interpolation, based on the evaluated result of said evaluating means; and means for reconstructing the distribution of X-ray attenuation coefficients of said object.

23. An apparatus for cone-beam X-ray computed tomography as claimed in claim 22, wherein if on the plane of said two-dimensional X-ray detector for detecting said projection data a u axis is set to the rotating direction of said scanner, a v axis is set in parallel to the center axis of rotation of said scanner, and said prepared correction table of said projection in the k direction is represented by U(u, v, k) and V(u, v, k) (k=1, 2, ..., $N_k$, u=1, 2, ..., $N_i$, v=1, 2, ..., $N_j$), said evaluating means comprises means for calculating a correlation between said prepared correction tables adjacent to each other in said k direction for evaluating continuity of said prepared correction tables adjacent to each other.

24. An apparatus for cone-beam X-ray computed tomography as claimed in claim 22, if k is any natural number, said evaluating means comprises means for calculating valU(u, v, k) and valV(u, v, K) (if k+l is overflown out of the range of k=1, 2, ..., $N_k$ in the calculation, the tail of k is circulated to the head of k.) according to the expression of;

$$valU(k) = \sum_{v=1}^{N_j} \sum_{u=1}^{N_i} \sum_{l=-p}^{p} (U(u,v,k+l) - \overline{U}(u,v,k))^2$$

$$valV(k) = \sum_{v=1}^{N_j} \sum_{u=1}^{N_i} \sum_{l=-p}^{p} (V(u,v,k+l) - \overline{V}(u,v,k))^2$$

where $$\overline{U}(u,v,k) = \frac{1}{2p+1} \sum_{l=-p}^{p} U(u,v,k+l)$$

$$\overline{V}(u,v,k) = \frac{1}{2p+1} \sum_{l=-p}^{p} V(u,v,k+l).$$

25. An apparatus for cone-beam X-ray computed tomography as claimed in claim 22, wherein if on the plane of said two-dimensional X-ray detector for detecting said projection data a u axis is set to the rotating direction of said scanner, a v axis is set in parallel to the center axis of rotation of said scanner, and said prepared correction table of said projection in the k direction is represented by U(u, v, k) and V(u, v, k) (k=1, 2, ..., $N_k$, u=1, 2, ..., $N_i$, v=1, 2, ..., $N_j$), said evaluating means comprises means for calculating a correlation between said prepared correction tables adjacent to each other in said k direction for evaluating continuity of said prepared correction tables adjacent to each other, and wherein it is determined if the values calculated by said evaluating means meet a specific condition.

26. An apparatus for cone-beam X-ray computed tomography as claimed in claim 22, wherein if on the plane of said two-dimensional X-ray detector for detecting said projection data a u axis is set to the rotating direction of said scanner, a v axis is set in parallel to the center axis of rotation of said scanner, and said prepared correction table of said projection in the k direction is represented by U(u, v, k) and V(u, v, k) (k=1, 2, ..., $N_k$, u=1, 2, ..., $N_i$, v=1, 2, ..., $N_j$), said evaluating means comprises means for calculating a correlation between said prepared correction tables adjacent to each other in said k direction for evaluating continuity of said prepared correction tables adjacent to each other, and wherein it is determined if the values calculated by said evaluating means are greater than a specific threshold value.

27. An apparatus for cone-beam X-ray computed tomography as claimed in claim 22, wherein if k is any natural number, said evaluating means comprises means for calculating valU(u, v, k) and valV(u, v, k) (if k+l is overflown out of the range of k=1, 2, . . . , $N_k$ in the calculation, the tail is circulated to the head of k) according to the expression of:

$$valU(k) = \sum_{v=1}^{N_j} \sum_{u=1}^{N_i} \sum_{l=-p}^{p} (\overline{U}(u,v,k+l) - \overline{U}(u,v,k))^2$$

$$valV(k) = \sum_{v=1}^{N_j} \sum_{u=1}^{N_i} \sum_{l=-p}^{p} (\overline{V}(u,v,k+l) - \overline{V}(u,v,k))^2$$

where $$\overline{U}(u,v,k) = \frac{1}{2p+1} \sum_{l=-p}^{p} U(u,v,k+l)$$

$$\overline{V}(u,v,k) = \frac{1}{2p+1} \sum_{l=-p}^{p} V(u,v,k+l),$$

and wherein if the value calculated by said evaluating means is greater than a specific threshold value of said projection in the serial k (=$k_0$, $k_0$+1, . . . , $K_0$+n) direction, said prepared correction table of said projection in the direction of k=$k_0$+1, . . . , k=$k_0$+n−1 is deleted from said means for saving correction table, and said interpolating means operates to derive the correction table of said projection in the direction of k=$k_0$+1, . . . , k=$k_0$+n−1 from said prepared correction table in said $k_0$ and said ($k_0$+n) directions through the effect of the interpolation.

28. An apparatus for cone-beam X-ray computed tomography as claimed in claim 27, wherein said interpolating means comprises means for deriving said prepared correction table U(u, v, k) and V(u, v, k) (k=$k_0$+1, . . . , $k_0$+n−1, $k_1$<$k_0$+1, $k_0$+n−1<$k_2$) deleted from said means for saving correction table from said prepared correction table U(u, v, $k_1$) and V(u, v, $k_1$) immediately before said deleted correction table in said projection direction and said prepared correction table U(u, v, $k_2$) and V(u, v, $k_2$) immediately after said deleted correction table in said projection direction according to the expression of;

$$U(u,v,k) = \frac{k_2 - k}{k_2 - k_1} \cdot U(u,v,k_1) + \frac{k - k_1}{k_2 - k_1} \cdot U(u,v,k_2)$$

$$V(u,v,k) = \frac{k_2 - k}{k_2 - k_1} \cdot V(u,v,k_1) + \frac{k - k_1}{k_2 - k_1} \cdot V(u,v,k_2).$$

29. A method for cone-beam X-ray computed tomography in which a scanner mounting an X-ray source for applying a cone-beam X ray and a scanner having a two-dimensional X-ray detector for detecting an X-ray is rotated around an object to measure omnidirectional projection data around said object, an image geometric distortion of said projection data is corrected by referring a correction table, and a distribution of X-ray attenuation coefficients is reconstructed by using said distortion-corrected projection data, comprising the steps of:

preparing said correction table in advance and saving said table in means for saving correction table;

calculating an evaluation function for evaluating continuity of said prepared correction table between the previous and the subsequent projections of a subject projection for obtaining said projection data;

deleting said prepared correction table that is not continuously changed between the previous and the subsequent projections from said means for saving correction table based on the calculated value of said evaluation function, replacing said correction table that is not continuously changed with a correction table obtained by interpolating said prepared correction tables of the previous and the subsequent projections, and saving the replaced correction table in said means for saving correction table;

detecting a location of a view field boundary of said two-dimensional X-ray detector from said distortion-corrected projection data by using the correction table saved in said means for saving correction table; and extrapolating projection data of a predetermined width from said location of the view field boundary detected in the step of detecting; and reconstructing said X-ray attenuation coefficients distribution from the projection data extrapolated in the step of extrapolating.

30. An apparatus for X-ray computed tomography having a scanner mounting an X-ray source for applying a cone-beam X ray and a two-dimensional X-ray detector for detecting an X-ray, means for rotating said scanner around an object, means for measuring omnidirectional projection data around said object, and means for measuring omnidirectional projection data around said object, for reconstructing an X-ray attenuation distribution, comprising:

means for preparing a correction table on which an image geometric distortion of said projection data is corrected, said preparing means having means for preparing said correction table of each projection for obtaining said projection data in advance and means for saving said prepared correction table;

evaluating means for calculating an evaluation function for evaluating continuity of said correction table between the previous and the subsequent projections of each subject projection for obtaining said projection data and comparing the calculate value of said evaluation function with a predetermined threshold value for evaluating said prepared correction table;

interpolating means for replacing said prepared correction table that is not continuously changed between said previous and subsequent projections with a correction table interpolated from the prepared correction tables of said previous and subsequent projections, based on the evaluating result of said evaluation function;

means for correcting an image geometric distortion of said projection data by referring to said correction table;

means for detecting a location of a view field boundary of said two-dimensional X-ray detector about said distortion-corrected projection data;

extrapolating means for generating said projection data of a predetermined width from said location of the view field boundary detected by said detecting means; and means for reconstructing said X-ray attenuation distribution of said object from said projection data extrapolated in said extrapolating means.

* * * * *